United States Patent [19]

Stüber

[11] Patent Number: 4,927,809
[45] Date of Patent: May 22, 1990

[54] OLIGOPEPTIDYL NITRILE DERIVATIVES, AGENTS CONTAINING THEM AND THEIR USE

[75] Inventor: Werner Stüber, Lahntal, Fed. Rep. of Germany

[73] Assignee: Behringwerke Aktiengesellschaft, Marburg/Lahn, Fed. Rep. of Germany

[21] Appl. No.: 19,122

[22] Filed: Feb. 26, 1987

[30] Foreign Application Priority Data

Feb. 28, 1986 [DE] Fed. Rep. of Germany ....... 3606480

[51] Int. Cl.[5] ...................... A61K 31/19; A61K 31/40; C07C 119/00; C07D 207/00
[52] U.S. Cl. ......................................... 514/20; 514/11; 514/17; 514/18; 514/19; 548/532; 548/533; 558/393
[58] Field of Search ..................... 558/393; 514/11, 17, 514/18, 19, 20; 548/532, 533

[56] References Cited

FOREIGN PATENT DOCUMENTS 0298568 12/1987 Japan .................................... 558/393

OTHER PUBLICATIONS

"Inhibition of Serine Proteases by Low Molecular Weight Peptides and Their Derivatives", Jawed Fareed et al., Annals New York Academy of Sciences, (1981), 370, pp. 765-784.

"Identification of Asparaginyl and Glutaminyl Residues in Endo Position in Peptides by Dehydration-Reduction", Charlotte Ressler et al., Journal of the American Chemical Society, (1966), 88, pp. 2025-2035.

*Primary Examiner*—Mary C. Lee
*Assistant Examiner*—J. Richter
*Attorney, Agent, or Firm*—Finnegan, Henderson, Farabow, Garrett and Dunner

[57] ABSTRACT

Compounds of the formula I

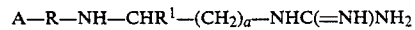

$$A-R-NH-CHR^1-(CH_2)_a-NHC(=NH)NH_2$$

in which
  $R^1$ is the cyanide group,
  R is Pro or D—Phe—Pro,
  A is a hydrogen atom or a protective group customary in peptide chemistry, and
  a is an integer from 2 to 5, preferably 3 or 4, which are able to inhibit serine proteases, and a process for their preparation, are described.

Agents containing compounds of this type can be used as anticoagulants.

5 Claims, No Drawings

OLIGOPEPTIDYL NITRILE DERIVATIVES, AGENTS CONTAINING THEM AND THEIR USE

The invention relates to oligopeptidyl nitrile derivatives, to the synthesis and use of these compounds, and to pharmaceutical agents which contain these compounds acting as inhibitors of serine proteases. The term oligopeptidyl nitrile derivatives is used to designate derivatives of an alpha-amino acid whose carboxyl group has been replaced by a cyanide group and whose amino group is substituted with an alpha-aminoacyl or a peptidyl group. It is known that a large number of pathophysiological conditions result in a consumption of AT III, which is the most important thrombin inhibitor in human plasma, with the formation of a thrombin-AT III complexes. There is an increased risk of thrombosis when the AT III level falls to below 75 % of normal. The therapy of acquired and hereditary AT III deficiency is effected by administration of AT III obtained from the plasma of blood donors. There are limits to this therapy by reason of the restricted availability of human plasma. For this reason, it is desirable to replace the naturally occurring thrombin inhibitor by synthetic compounds which are able to suppress or slow down the blood clotting process. The current state of knowledge is that synthetic inhibitors of this type are substrates which are able to block the specificity cavity of a protease and thus reduce its activity. Suitable for this purpose are peptide derivatives of arginine, because these are able to fit well in the specificity cavity of serine proteases. The peptide sequence D-Phe-Pro-Arg has proved to be particularly favorable, this particularly inhibiting thrombin. In this context, particular importance attaches to derivatization of the C-terminal end of the arginine, as this greatly influences the efficacy of these protease inhibitors (Annals of the New York Academy of Science (1981), 370, 765-784). It is known that derivatives of this type act as potent serine protease inhibitors when the C-terminal end of the peptide is a reactive group. The formyl group and the chloromethylcarbonyl group on arginine have proved to be very active. Other known compounds acting as thrombin inhibitors are structurally related to arginine, for example agmatine derivatives or N-alpha-arylsulfonyl-p-guanidinophenylalaninamides. It has now been found, surprisingly, that compounds of the formula I

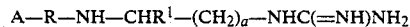

A—R—NH—CHR$^1$—(CH$_2$)$_a$—NHC(=NH)NH$_2$     I in which
R$^1$ the cyanide group,
R is Pro or D-Phe-Pro,
A is a hydrogen atom or a protective group customary in peptide chemistry, and
a is an integer from 2 to 5, preferably 3 or 4,
are able to inhibit serine proteases.

Hence the invention relates to a compound of the formula I with the indicated definitions, and to its physiologically tolerated salts. The compounds according to the invention are synthesized fragment-wise or stepwise by methods customary in peptide chemistry using suitably protected amino acid derivatives with the aid of temporary protective groups. Where appropriate, the protective groups are eliminated and salts are prepared. The cyanide group is obtained by elimination of water from a corresponding amide (J. Amer. Chem. Soc. (1966) 88, 2025-2035). The invention also relates to a process for the preparation of a compound of the formula I with the indicated definitions, which comprises conversion of a compound of the formula I in which R$^1$ is (CONH$_2$), with the aid of a watereliminating agent, into the corresponding nitrile form, or comprises conversion of a compound of the formula I in which R is a bond and R$^1$ is (CONH$_2$), using a watereliminating agent, into a compound of the formula I in which R$^1$ is the cyanide group, and, where appropriate after removal of the protective groups, reaction with a compound of the formula A-R-X in which X is an activating group, or comprises conversion of a compound of the formula I in which R is Pro and R$^1$ is (CONH$_2$), using a watereliminating agent, into a compound of the formula I in which R$^1$ is the cyanide group, and, after elimination of the protective group, preparation of a compound of the formula I by an acylation reaction with a protected activated derivative of D-Phe. The invention likewise relates to a process for the preparation of a compound of the formula I with the indicated definitions, which comprises subjecting a compound of the formula I in which R$^1$ is (CONH$_2$) to a watereliminating reaction at the carboxamide group, with the aid of a watereliminating agent, or converting a compound of the formula I in which R is a bond and R$^1$ is CONH$_2$) and A is a protective group customary in peptide chemistry, by water elimination at the carboxamide group, into the corresponding cyanide compound, and, after elimination of the protective group, reacting with a compound of the formula A-R-X, in which X represents an activating group, to give a compound of the formula I. The carboxamide group can be converted into the cyanide group at any desired stage of the synthesis, i.e. at the tripeptide, dipeptide or amino acid carboxamide stage The starting material which is preferably used is L-argininamide, whose guanidino group is preferably protonated. Peptide synthesis and the introduction of protective groups are carried out by standard methods of peptide chemistry as described by, for example, M. Bodanszky, Principles of Peptide Synthesis, published by Springer, Berlin-HeidelbergNew York-Tokyo 1984. The coupling reactions are preferably carried out in solution by activating a C-terminal carboxyl group with a carbodiimide, preferably dicyclohexylcarbodiimide, in the presence of an acidic compound such as 1-hydroxybenzotriazole, and allowing it to react with an amino group in the presence of an organic base with the formation of a peptide bond. In this way, preferably Boc-D-Phe-Pro, Fmoc-D-Phe-Pro, Z-D-Phe-Pro or Fmoc-Pro are coupled to the amino group of L-argininamide. Apart from argininamide derivatives prepared in this way, which are suitable for conversion into the corresponding nitriles, it is also possible to convert argininamide derivatives which are provided with a temporary protective group on the alpha-amino group into the nitrile. The Boc group is preferably used as the temporary protective group, in which case after the water-elimination reaction the nitrile produced by removal of this protective group is able to couple and can be reacted to give the desired compounds. The amides are converted into the nitriles using dehydrating reagents, for example using thionyl chloride in dimethylformamide, but preferably using phosphorus oxychloride in pyridine. In a particularly preferred embodiment of the dehydration, 1 mol of amide is reacted with 1.1 mol of phosphorus oxychloride in the presence of 2 mol of imidazole in pyridine. The reaction temperature during the addition of phosphorus oxychloride is preferably kept in the range −25 to −15° C. The reaction is then brought to completion by stirring the mixture at room temperature for 30 minutes to 5 hours, preferably one hour. The products are isolated by purification methods customary in peptide chemistry, preference being given to partition of the crude products between organic solvents and water and use of column chromatography. The nitrile derivatives prepared in this way exhibited the correct composition in the analyses which were carried out. Thus, the nitrile triple bonds were found in the expected region of the infra red spectrum at about 2250 cm$^-$ Nuclear magnetic resonance investigations showed the presence of a nitrile group in the $^{13}$C NMR spectrum at about 119 ppm. In the case of nitrile derivatives of the formula I in which R is D-Phe-Pro and A is a protective group, it is possible to eliminate protective groups of the urethane type, Boc and Fmoc being preferred, using the customary reagents to expose the N-terminal amino group. The Boc group is preferably eliminated with 1.2 N HCl in glacial acetic acid or with 50% trifluoroacetic acid in methylene chloride, and the Fmoc group is eliminated with piperidine in methylene chloride. The compounds according to the invention surprisingly exhibit a potent inhibitory action against serine proteases. This action is preferentially exhibited against thrombin. The specificity with respect to other enzymes, for example F Xa, is influenced by groups at the N-terminal end.

The compounds according to the invention are suitable as substitutes for naturally occurring serine protease inhibitors, preferably of AT III. These substances and their physiologically tolerated salts can be used as agents for abolishing AT III deficiency, by which means the risk of thrombosis is reduced or eliminated. These agents can additionally contain physiologically acceptable vehicles or auxiliaries.

ABBREVIATIONS

| | |
|---|---|
| AT III | Antithrombin III |
| Z | Benzyloxycarbonyl |
| Boc | tert.-Butyloxycarbonyl |
| Fmoc | 9-Fluorenylmethyloxycarbonyl |
| NMR | Nuclear magnetic resonance |
| TLC | Thin-layer chromatography |
| $R_F$ | Retention factor |
| C/T | Chlorine/4,4-bis(dimethylamino)diphenylmethane test |
| UV | Ultraviolet visualization |
| DCU | Dicyclohexylurea |
| DCC | Dicyclohexylcarbodiimide |
| HOBt | Hydroxybenzotriazole |
| DMF | Dimethylformamide |
| NMM | N-Methylmorpholine |

| Mobile phases for thin-layer chromatography: | | |
|---|---|---|
| (A) | n-Butanol/glacial acetic acid/water | 3:1:1 |
| (B) | Chloroform/methanol/glacial acetic acid | 50:20:5 |

EXAMPLE 1

N(alpha)-Boc-D-Phenylalanyl-L-prolyl-L-(1-amino-4-guanidino)valeronitrile

1. N(alpha)-Boc-D-Phenylalanyl-L-prolyl-L-argininamide 6.6 g of Boc-D-Phe-Pro (18 mmol) and 2.43 g of HOBt were dissolved in 100 ml of DMF, and the solution was cooled to 0° C. and 3.8 g of DCC were added. The mixture was stirred at 0° C. for 30 minutes and at room temperature for 30 minutes. Then 5.28 g of Arg-NH$_2$ × 2 CH3COOH and 3.8 ml of NMM were added. After 12 hours, the precipitated DCU was removed by filtration with suction, the solvent was removed by evaporation in vacuo, and the residue was taken up in chloroform. The organic phase was extracted by shaking three times with saturated sodium bicarbonate solution and three times with saturated sodium chloride solution. The chloroform solution was dried over sodium sulfate and concentrated in vacuo. The peptide derivative was obtained as crystals by dropwise addition of the concentrated chloroform solution to diethyl ether. The crystals were dried over phosphorus pentoxide under high vacuum.

Yield: 7.3 g (70% of theory)
Purity check: TLC $R_F$ = 0.46 (A)

N(alpha)-Boc-D-Phenylalanyl-L-prolyl-L-(1-amino-4-guanidino)valeronitrile 4 g of the amide prepared in 1. and 1 g of imidazole were dissolved in 60 ml of pyridine. 2.8 ml of phosphorus oxychloride were added dropwise at −20° C. The mixture was then stirred at room temperature for 1 hour, concentrated in vacuo, and the residue was taken up in chloroform. The organic phase was extracted three times with water and dried over sodium sulfate. The peptide derivative was crystallized by dropwise addition to diethyl ether, and was washed with ether and dried under high vacuum.

Yield: 2.6 g (69% of theory)
Purity check: TLC $R_F$ = 0.61 (A)
Melting point: decomposition above 75° C.

EXAMPLE 2

N(alpha)-Fmoc-D-Phenylalanyl-L-prolyl-L-(1-amino-4-guanidino)valeronitrile

1. N(alpha)-Fmoc-D-Phenylalanyl-L-prolyl-L-argininamide 1.45 g of Fmoc-D-Phe-Pro (3 mmol) and 405 mg of HOBt were dissolved in 40 ml of DMF and, at 0oC, 630 mg of DCC were added, and then the mixture was stirred at 0oC for 30 minutes and at room temperature for 30 min. Then 880 mg of Arg-NH$_2$ × 2 CH3COOH and 630 pl of NMM were added. After 12 hours, insolubles were filtered off, the DMF was evaporated off, and the oily residue was taken up chloroform. The organic phase was extracted by shaking three times with saturated sodium bicarbonate solution and three times with saturated sodium chloride solution, and was dried over sodium sulfate. After the chloroform had been evaporated off, a pure product was obtained.

Yield: 900 mg (43%)
Purity check: TLC $R_F$ = 0.34 (B)

2. N(alpha)-Fmoc-D-Phenylalanyl-L-prolyl-L-(1-amino-4guanidino)valeronitrile 770 mg of the product synthesized in 1. were dissolved in 10 ml of pyridine, 100 mg of imidazole were added, and the mixture was cooled to −20° C. 0.5 ml of phosphorus oxychloride was added dropwise, and the mixture was stirred at room temperature for one hour. It was then evaporated to dryness in vacuo, and the residue was taken up in chloroform. This solution was extracted by shaking with a saturated sodium bicarbonate solution and a saturated sodium chloride solution, three times each. It was dried over sodium sulfate. After partial concentration of the solution in vacuo, the product was crystallized by dropwise addition to ether ethyl acetate (2:1),filtered off and dried under high vacuum.

Yield: 380 mg (52.5%)
Purity check: TLC $R_F$ = 0.62
Melting point: decomposition above 125° C

EXAMPLE 3

H-D-Phenylalanyl-L-prolyl-L-(1-amino-4-guanidino)-valeronitrile ditrifluoroacetate 0.5 ml of anisole and 3 ml of trifluoroacetic acid were added to 270 mg of the product prepared as in Example 1, and the mixture was maintained at room temperature for 5 minutes with exclusion of moisture. The product was crystallized by dropwise addition to diethyl ether. It was removed by centrifugation, washed with diethyl ether, and taken up in water. The aqueous phase was extracted three times with diethyl ether and was freeze-dried. A fluffy white powder was obtained.

Yield: 170 mg (54%)
Purity check: TLC RF = 0.275 (A)

FUNCTION TESTS

The activity of the substances prepared as in Examples 1, 2 or 3 was ascertained by determination of the thrombin time. This entailed the concentration (in $\mu$mol/l) which doubled the thrombin time being ascertained.

TEST PROCEDURE

50 $\mu$l of inhibitor solution of various concentrations, 50 $\mu$l of standard human plasma and 100 $\mu$l of diethylbarbituric acid/sodium acetate buffer, pH 7.6, were incubated at 37° C. for 45 seconds and 100 $\mu$l of alpha human thrombin (3.0 IU/ml) were added. The tests were carried out on a Schnitger & Gross apparatus for determination of the thrombin time.

TABLE 1

| Compound according to Example | Doubling of the thrombin time at concentration (in $\mu$mol/l final conc.) |
| --- | --- |
| 1 | 3.66 |
| 2 | 3.66 |
| 3 | 1.1 |

TOXICITY TESTS

The toxicity of H-D-Phe-Pro-Arg-CN × 2HCOOH gated in an animal model. The test substance was administered i.v. to mice. Clinically detectable pathological findings were found at and above a dose of 50 mg/kg. The dose for a therapeutic effect ought to be about 1–4 mg/kg.

Inhibition constant ($K_i$) of H-D-Phe-Pro-Arg-CN × 2HCOOH: Ki $H_i$ = 6 × $10^{-7}$ mol/l (alpha human thrombin)

I claim:

1. A compound of the formula I $$A-R-NH-CHR^1-(CH_2)_a-NHC(=NH)NH_2 \quad I$$

in which
$R^1$ is the cyanide group,
R is Pro or D-Phe-Pro,
A is a hydrogen atom or a protective group customary in peptide chemistry, and
a is an integer from 2 to 5, preferably 3 or 4,
and its physiologically tolerated salts.

2. A compound as claimed in claim 1, in which A-R is Boc D-Phe-Pro, Fmoc-D-Phe-Pro, Z-D-Phe-Pro or Fmoc-Pro.

3. D-Phenylalanyl-L-prolyl-L-(1-amino-4-guanidino)valeronitrile, its derivative provided at the N-terminal end with protective groups customary in peptide chemistry, and its physiologically tolerated salts.

4. A pharmaceutical composition for the treatment of diseases related to disorders of the coagulating system were there is an increased tendency of the blood to coagulate which comprises an effective amount for said treatment of a compound of the formula I as claimed in claim 1, together with a pharmaceutically acceptable vehicle.

5. A method for the treatment of diseases relating to disorders of the coagulating system where there is an increased tendency of the blood to coagulate in a patient which comprises administering an effective amount of a compound of the formula I as claimed in claim I.

* * * * *